(12) United States Patent
Siedenburg

(10) Patent No.: US 9,052,398 B2
(45) Date of Patent: Jun. 9, 2015

(54) LIQUID MIXTURE USED TO TEST AND VALIDATE TEST DEVICES

(71) Applicant: Smiths Heimann GmbH, Wiesbaden (DE)

(72) Inventor: Uwe Siedenburg, Essenheim (DE)

(73) Assignee: SMITHS HEIMANN GmbH, Wiesbaden (DE)

( * ) Notice: Subject to any disclaimer, the term of this patent is extended or adjusted under 35 U.S.C. 154(b) by 0 days.

(21) Appl. No.: 14/187,916

(22) Filed: Feb. 24, 2014

(65) Prior Publication Data

US 2014/0166936 A1  Jun. 19, 2014

Related U.S. Application Data

(63) Continuation of application No. PCT/EP2012/065951, filed on Aug. 15, 2012.

(30) Foreign Application Priority Data

Aug. 22, 2011 (DE) .......................... 10 2011 081 328
Nov. 10, 2011 (DE) .......................... 10 2011 118 094

(51) Int. Cl.
  *G01T 7/00* (2006.01)
  *G01V 5/00* (2006.01)
  *C07C 31/22* (2006.01)
  *G01N 23/06* (2006.01)

(52) U.S. Cl.
  CPC .............. *G01T 7/005* (2013.01); *G01V 5/0008* (2013.01); *G01N 2223/3037* (2013.01); *C07C 31/225* (2013.01); *G01N 23/06* (2013.01)

(58) Field of Classification Search
  CPC ................................................... G01N 33/22
  USPC ................................ 436/8, 57, 131; 422/68.1
  See application file for complete search history.

(56) References Cited

U.S. PATENT DOCUMENTS

| | | | |
|---|---|---|---|
| 2,495,277 A | 1/1950 | Navikas | |
| 4,190,056 A * | 2/1980 | Tapper et al. | 600/307 |
| 5,958,299 A | 9/1999 | Kury et al. | |
| 6,839,406 B2 | 1/2005 | Ries et al. | |
| 7,583,221 B2 | 9/2009 | Detlefsen et al. | |
| 8,563,316 B2 * | 10/2013 | Duffy et al. | 436/8 |
| 2004/0021757 A1 * | 2/2004 | Shastry et al. | 347/106 |

FOREIGN PATENT DOCUMENTS

| | | |
|---|---|---|
| DE | 199 54 662 | 6/2001 |
| DE | 10 125 531 | 11/2002 |
| DE | 10 2005 016 106 | 10/2006 |
| DE | 10 2011 081 328 | 2/2013 |
| GB | 347144 | 10/1929 |
| WO | WO 2005/094768 A1 | 10/2005 |
| WO | WO 2009/136677 A1 | 11/2009 |

OTHER PUBLICATIONS http://stainsfile.info/StainsFile/prepare/preserve/preservative-glycerol.htm, updated Dec. 2010.*
Sorby et al., "Dielectric Constants of Complex Pharmaceutical Solvent Systems I," J. of Pharma. Sci., vol. 52, No. 12, pp. 1149-1153 (Dec. 1, 1963).
Cox et al., "A Continuous-Flow, Rapid-Mixing, Photolabelling Technique Applied to the Acetylcholine Receptor," Analytical Biochemistry, vol. 136, No. 2, pp. 476-486 (Feb. 1, 1984).
Le Roux et al., "Preserving the Neurovascular Supply in the Hall-Findlay Superomedial Pedicle Breast Reduction: An Anatomical Study," J. of Plastic, Reconstructive & Aesthetic Surgery, vol. 63, pp. 655-662 (2010).
Herzen et al., "Quantitative Phase-Contrast Tomography of a Liquid Phantom Using a Conventional X-Ray Tube Source," Optics Express, Optical Soc. of Am., vol. 17, No. 12, pp. 10010-10018 (2009).

* cited by examiner

*Primary Examiner* — Jill Warden
*Assistant Examiner* — Julie Tavares
(74) *Attorney, Agent, or Firm* — Muncy, Geissler, Olds & Lowe, P.C.

(57) ABSTRACT

The invention relates to a liquid mixture used to test and validate test devices for inspecting objects or persons, said mixture containing glycerol and comprising a mixture of glycerol, ethanol and water.

2 Claims, No Drawings

LIQUID MIXTURE USED TO TEST AND VALIDATE TEST DEVICES

This nonprovisional application is a continuation of International Application No. PCT/EP2012/065951, which was filed on Aug. 15, 2012, and which claims priority to German Patent Application No. 10 2011 081 328.4, which was filed in Germany on Aug. 22, 2011 and German Patent Application No. 10 2011 118 094.3, which was filed in Germany on Nov. 10, 2011, and which are all herein incorporated by reference.

BACKGROUND OF THE INVENTION

1. Field of the Invention

The invention relates to a liquid mixture used to test and validate test devices for inspecting objects or persons, said mixture containing glycerol and having a mixture of glycerol, ethanol and water 2. Description of the Background Art German patent application DE 10 2011 081 328.4 describes the use of inspection systems, in which the persons or objects to be inspected are x-rayed or irradiated in screening devices by electromagnetic rays, for inspecting persons and objects, such as luggage, for hazardous materials such as blasting materials or explosives. As is generally known, such inspection systems are used at airports for inspecting passengers and luggage.

The inspection systems according to a known embodiment contain screening devices in which the objects to be inspected, for example, luggage, are x-rayed or irradiated by x-rays and the transmitted or scattered x-rays are detected and analyzed (DE 10125531-A, DE 19954662-A).

Screening devices are known for inspecting persons, in which the persons to be inspected are irradiated with electromagnetic mm waves and the scattered mm waves are analyzed to obtain an image (DE 102005016106-A).

The screening devices must be tested and validated before being placed into operation. This typically occurs with real hazardous materials, therefore the explosives to be detected. The use of explosives is regulated by law, and moreover they are difficult to handle.

U.S. Pat. No. 5,958,299 discloses an explosive simulation mixture, which contains non-explosive components, whereby the components are selected so that the mixture has a physical form, density, x-ray transmission, and an effective atomic number that corresponds to a selected explosive mixture. An x-ray screening device can be tested for the detection of the specific explosive with the use of the simulation mixture instead of a real explosive. Solid, plastic, and gel-like compositions, which are made up of different components, are described as simulation mixtures.

Inspection systems are increasingly required to detect liquid explosives and so-called "home-made explosives" as well. The object of the invention therefore is to provide such a mixture that simulates blasting materials or explosives and is not explosive, non-critical in regard to handling, and economic to produce, and behaves like the real hazardous material in a screening device for inspecting objects or persons.

In DE 10 2011 081 328.4, a mixture of glycerol, sodium hydroxide (NaOH), and water is used as the simulation mixture, whereby glycerol and sodium hydroxide are present in a weight ratio of glycerol/sodium hydroxide between 6.5 and 3.8.

SUMMARY OF THE INVENTION

It is therefore an object of the invention to provide a liquid mixture for testing and validating screening devices for inspecting objects or persons, said mixture containing glycerol, characterized in that it consists of a mixture of glycerol, ethanol, and water.

DETAILED DESCRIPTION

According to an exemplary embodiment of the invention, a mixture of glycerol, ethanol, and water is used for simulating explosive liquids. In this case, the amount of glycerol in the mixture is preferably 33.7% by weight to 48.2% by weight, particularly about 41.2% by weight. The amount of ethanol ($C_2H_5OH$) is preferably 48.272% by weight to 62.272% by weight, particularly about 55.272% by weight. The mixture is brought to 100% by weight with water.

A preferred mixture has 41.2% by weight of glycerol, 55.272% by weight of ethanol ($C_2H_5OH$), and 3.528% by weight of water.

Screening devices intended to detect liquid hazardous materials are tested and validated with this mixture. During the validation it is checked whether the inspection system meets the predefined requirements.

For testing and validating, the liquid simulation mixture according to the invention is placed in an object to be inspected or on a person. The simulation mixture consists of glycerol, ethanol, and water.

The previously described basic formulation can be diluted or thickened with retention of the ratios between glycerol and ethanol by more or less water, whereby the total mixture remains liquid. Simulation mixtures for simulating various liquid hazardous materials can be produced by the different amounts of water.

The objects to be inspected, particularly luggage, are x-rayed or irradiated with electromagnetic rays in the screening devices. The transmitted or scattered rays are detected and analyzed.

A preferred use of a mixture according to an embodiment of the invention is the testing and validating of x-ray screening devices for inspecting persons or objects, particularly luggage, as they have been described as prior in the art in the introduction to the description.

Likewise, the simulation mixture according to the invention can be used to test and validate screening devices in which electromagnetic mm waves are used to inspect persons or objects.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A liquid mixture for testing and validating screening devices for inspecting objects or people, the mixture consisting of glycerol, ethanol, and water,
    wherein an amount of glycerol is 33.7% by weight to 48.2% by weight, the amount of ethanol is 48.272% by weight to 62.272% by weight the remaining amount to 100% by weight is water.

2. The liquid mixture according to claim 1, wherein an amount of glycerol is 41.2% by weight and the amount of ethanol is 55.272% by weight.

* * * * *